United States Patent [19]

Murata

[11] Patent Number: 5,093,617
[45] Date of Patent: Mar. 3, 1992

[54] HALL-EFFECT SENSOR HAVING INTEGRALLY MOLDED FRAME WITH PRINTED CONDUCTOR THEREON

[75] Inventor: Shigemi Murata, Himeji, Japan

[73] Assignee: Mitsubishi Denki K.K., Tokyo, Japan

[21] Appl. No.: 493,526

[22] Filed: Mar. 14, 1990

[30] Foreign Application Priority Data

| Mar. 14, 1989 | [JP] | Japan | 1-59539 |
| Mar. 15, 1989 | [JP] | Japan | 1-60706 |
| Mar. 15, 1989 | [JP] | Japan | 1-60707 |
| Mar. 15, 1989 | [JP] | Japan | 1-60708 |
| Mar. 15, 1989 | [JP] | Japan | 1-60709 |

[51] Int. Cl.⁵ ............ G01B 7/30; F02P 7/07
[52] U.S. Cl. ............ 324/235; 123/146.5 A; 123/617; 324/207.20
[58] Field of Search ...... 324/173, 174, 207.2, 324/207.21, 207.25, 235, 251, 252; 338/32 H; 323/368; 310/DIG. 3; 123/146.5 A, 617; 73/DIG. 3; 174/52.2

[56] References Cited

U.S. PATENT DOCUMENTS

| 4,011,476 | 3/1977 | Beard | 310/DIG. 3 X |
| 4,165,726 | 8/1979 | Helmer, Jr. | 123/617 X |
| 4,235,213 | 11/1980 | Jellissen | 123/617 X |
| 4,311,981 | 1/1982 | Luzynski | 323/368 X |
| 4,359,978 | 11/1982 | Brammer et al. | |
| 4,635,353 | 1/1987 | Tamagne | 123/617 X |
| 4,853,629 | 8/1989 | Rops | 324/251 X |
| 4,935,698 | 6/1990 | Kawaji et al. | 324/207.2 |

FOREIGN PATENT DOCUMENTS

0079281 5/1985 Japan ................ 324/251

OTHER PUBLICATIONS

Arnold et al; Hall Effect Detector and Miniswitch, IBM Tech. Discl. Bull., vol. 17, No. 11, Apr. 1975, p. 3220.

*Primary Examiner*—Gerard R. Strecker
*Attorney, Agent, or Firm*—Sughrue, Mion, Zinn, Macpeak & Seas

[57] ABSTRACT

A Hall-effect sensor, wherein a Hall element is disposed in a magnetic path being formed by a magnet and a flux guide, and the magnet, flux guide, and Hall element are integrally held with a molded frame, and the Hall element is fixed to the magnet (or flux guide) or the molded frame. This Hall-effect sensor can easily position the Hall element with higher sensitivity.

7 Claims, 5 Drawing Sheets

HALL-EFFECT SENSOR HAVING INTEGRALLY MOLDED FRAME WITH PRINTED CONDUCTOR THEREON

BACKGROUND OF THE INVENTION

1. Field of the Invention

The present invention relates to a Hall-effect sensor, for example, for use in detecting a crank angle for an ignition timing control apparatus for an internal combustion engine.

2. Description of Related Art

Recently, the Hall effect has been used for such various types of sensors as a position sensor, an angle sensor, and a speed sensor. As such a type of sensor using the Hall effect, there is well known a Hall-effect sensor in which a Hall element, a peripheral circuit such as an amplifier, a waveform shaping circuit, a surge protection element, and a magnetic circuit for generating a magnetic flux are integrally provided with each other by a resin. In addition to it, there is also well known a Hall IC in which a Hall element is fitted in a hybrid integrated circuit on a substrate made of ceramics. When such conventional Hall-effect sensors are manufactured, each of the Hall element, parts of the magnetic circuit and the like are positioned by use of jigs first, and then, a thermoplastic resin or a thermosetting resin is poured into a space surrounding each of them, following which being dried or hardened by a heater. As a result, there exist some problems that it is necessary to provide a lot of jigs for positioning such Hall element and parts in the sensor, that the positioning accuracy of those Hall element and parts is not so high that the sensor is not suitable for mass production, and that sensitivity of the sensor is inferior.

SUMMARY OF THE INVENTION

The foregoing problems are solved in accordance with the present invention. The Hall-effect sensor of the present invention comprises flux generating means for generating a magnetic flux and forming a magnetic path, a Hall element being disposed in this magnetic path, and a molded frame which holds both of the flux generating means and the Hall element integrally, the Hall element being fixed to the flux generating means or to the molded frame. A printed conductor for fetching a signal is also formed on the flux generating means or on the molded frame, and this printed conductor is electrically connected to the Hall element by connecting means. As a material for the connecting means, a bonding wire, solder or the like can be employed. The flux generating means concretely has a magnet and a flux guide, and it is desirable that this flux generating means forms a magnetic path by transmitting a magnetic flux being generated by the magnet to the flux guide. If the flux generating means is conductive, the Hall element is fixed to the flux generating means with an insulative film therebetween.

The Hall element may be a bare Hall chip, and the Hall chip may be a Hall IC, in which the Hall element is provided with a part of a peripheral circuit.

The Hall-effect sensor of the present invention can be used as a position sensor or a speed sensor, as well as an angle sensor for detecting a crank angle for ignition timing control for an internal combustion engine.

It is an object of the present invention to provide a Hall-effect sensor which can readily position the Hall element.

It is another object of the present invention to provide a Hall-effect sensor which has higher sensitivity.

It is a further object of the present invention to provide a Hall-effect sensor whose parts can readily and automatically be assembled.

The above and further objects and features of the invention will more fully be apparent from the following detailed description taken with the accompanying drawings.

DESCRIPTION OF THE PREFERRED EMBODIMENTS

Now, embodiments of the present invention will be described below with reference to the accompanying drawings. In each of such embodiments as will be described below, there will be described a sensor for detecting a crank angle of an internal combustion engine.

FIRST EMBODIMENT

Figure 1:
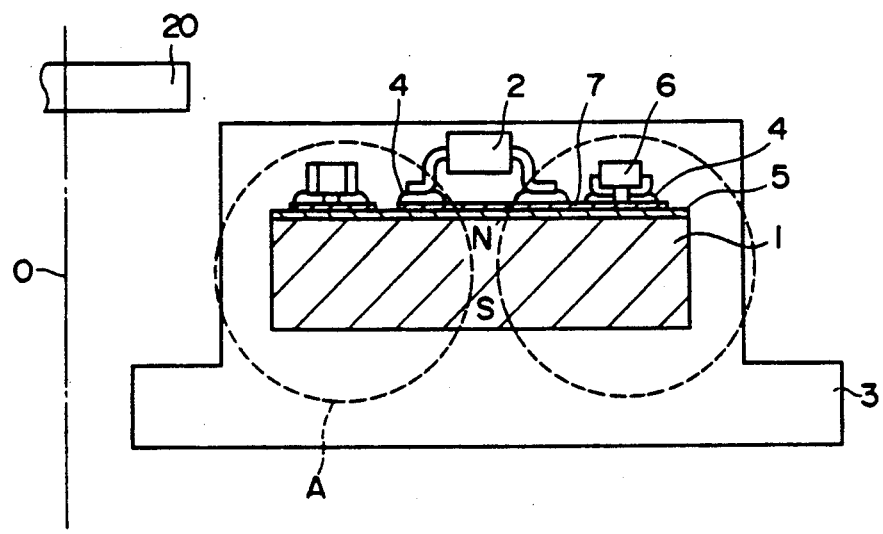
FIG. 1 is a sectional view of a Hall-effect sensor of a first embodiment of the present invention.

In FIG. 1, reference numeral 1 designates a flux generating member (magnet), which has a N pole and a S pole as shown in the figure. Onto the magnet 1, there is formed an insulative film 5 by means of evaporation, application or the like. On the insulative film 5, there is formed a printed conductor 7 with a predetermined pattern. There is arranged a Hall element 2 in a position above the magnet 1. The Hall element 2 is electrically connected to the printed conductor 7 by a soldering paste 4. As the Hall element 2, a bare Hall chip or a Hall IC may be employed, either of which being called the Hall element in this specification. There is provided such an electronic part 6 as a surge protection element on the insulative film 5 by the soldering paste 4. Such members constituting the sensor such as the magnet 1, insulative film 5, printed conductor 7, Hall element 2, soldering paste 4, and electronic part 6 are surrounded with a molded frame 3 made of a mold resin.

Figure 3:
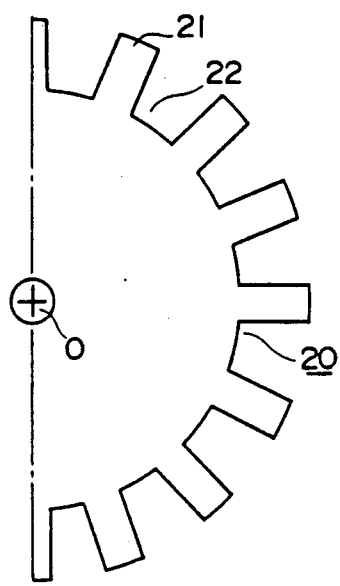
FIG. 3 is a plan view showing a flux shutter being used in embodiments of the present invention.

Reference numeral 20 designates a flux shutter as shown in FIG. 3. This flux shutter 20 is a magnetic material of a disk form, in which each of plural vanes 21 is provided to have a predetermined angle of radiation. When the flux shutter 20 is rotated around an axis O of rotation, the vane 21 and a space 22 which is defined in between the vanes move by turns in a position above the Hall element 2. When such a Hall-effect sensor as shown in FIG. 1 is employed as a crank angle sensor for internal combustion engine, the flux shutter 20 is rotated in synchronism with rotation of an internal combustion engine.

Figure 2:
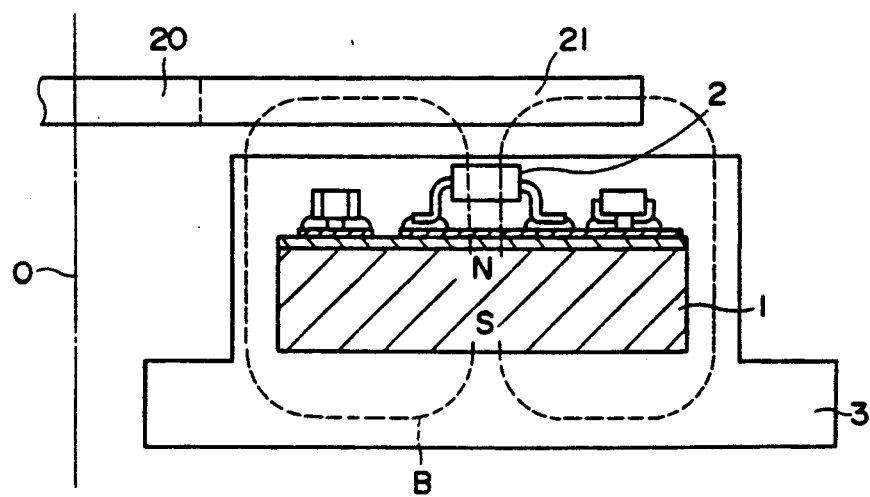
FIG. 2 is a sectional view for explaining the functional operation of the first embodiment shown in FIG. 1.

Now will be described below the operation of the sensor. When the space 22 of the flux shutter 20 is positioned above the Hall element 2 as shown in FIG. 1, a magnetic flux being generated by the magnet 1 forms such a magnetic path as shown by the broken line A. The magnetic flux being exerted upon the Hall element 2, thus is in the small state. On the other hand, when the vane 21 of the flux shutter 20 is positioned above the Hall element 2 as shown in FIG. 2, a magnetic flux being generated by the magnet 1 forms such a magnetic path as shown by the broken line B. The magnetic flux being exerted upon the Hall element 2, thus is in the large state. As can be seen from the above, such change of the magnetic flux in synchronism with the rotation of the internal combustion engine is given to the Hall element 2, and an electric signal corresponding to the change of the magnetic flux is generated according to the Hall effect. This electric signal is led to an outside circuit (not shown) via the printed conductor 7, and its waveform is processed so as to be used for detecting a crank angle.

Figure 4:
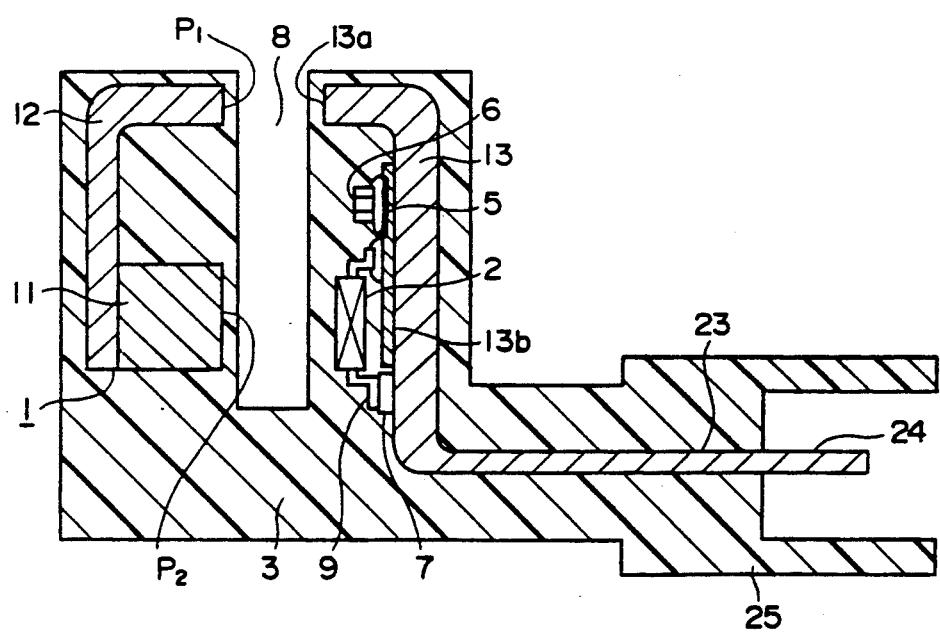
FIG. 4 is a sectional view of a Hall-effect sensor of one transformed example of the first embodiment of the present invention.

FIG. 4 shows another example of the first embodiment. In the figure, reference numeral 1 designates a flux generating member, which is comprised of a magnet 11, a flux guide 12 kept in contact with the magnet 11, and a flux guide 13 which is positioned to face in opposite directions of the magnet 11 and the flux guide 12 with a gap 8 between. A pole $P_1$ of the flux guide 12 and a pole $P_2$ of the magnet 11 which has a function opposite to the pole $P_1$ are arranged in the same direction. Portions of the flux guide 13 shown by 13a and 13b are positioned to face in opposite directions of the poles $P_1$ of the flux guide 12 and the $P_2$ of the magnet 11, respectively. This facing portion 13a is formed as one bent-end portion of the flux guide 13, and so is the facing portion 13b as a plane portion of the flux guide 13. There is applied the insulative film 5 onto the facing portion 13b. The flux guide 13 is provided with an insert conductor 23 for fetching an electric signal converted by the Hall element 2 to the outside, both of which are integrally formed with each other. The printed conductor 7 with a predetermined pattern is provided on the insulative film 5 and the insert conductor 23. This printed conductor 7 is electrically connected to the Hall element 2 by a lead wire 9 of the Hall element 2. There is provided an electronic part 6 such as a surge protection element on the insulative film 5 with the printed conductor 7 between. Members such as the flux generating member 1 and the Hall element 2 are integrally held by a molded frame 3 made of a mold resin. An end of the insert conductor 23 is projected from the molded frame 3 to be a connection pin 24. At one end of the molded frame 3, there is formed a connector 25 which connects the sensor to equipment and the like. When the mold is formed in this embodiment, after such each member such as the magnet 11, the flux guide 12, and the flux guide 13 to which the Hall element 2 is fixed are positioned, the molded frame 3 is adapted to be formed.

The operation of the sensor will be described below. Such a flux shutter 20 as shown in FIG. 3 moves in the gap 8. When the vane 21 of the flux shutter 20 is positioned in the gap 8, a magnetic flux being generated by the magnet 11 is shortened by the vane 21, and there is formed a magnetic path extending from the pole $P_1$ through the vane 21, pole $P_2$, magnet 11, flux guide 12, to the pole $P_1$. The magnetic flux exerted upon the Hall element 2, thus is in the small state. On the other hand, when the space 22 of the flux shutter 20 is positioned in the gap 8, a magnetic flux being generated by the magnet 11 is not shortened, and there is formed a magnetic path extending from the pole $P_1$ through the facing portion 13a, flux guide 13, facing portion 13b, Hall element 2, pole $P_2$, magnet 11, flux guide 12, to the pole $P_1$. The magnetic flux to exert upon the Hall element 2, then, is in the large state. As can be seen from the above, such change of the magnetic flux in synchronism with rotation of the internal combustion engine is given to the Hall element 2, and an electric signal corresponding to the change of the magnetic flux is generated according to the Hall effect. This electric signal is led to the outside circuit (not shown) via the printed conductor 7 and the insert conductor 23, and its waveform is processed to be used for detecting a crank angle.

As described above, in the first embodiment, the Hall element 2 is directly fixed to the flux generating member 1 (magnet 11 or flux guide 13), and it is not necessary to provide a jig for positioning the Hall element 2. When the Hall element 2 is fixed to the flux generating member 1 (magnet 1 or flux guide 13), such an art as packaging a circuit element onto a printed wiring board is employed, and thus higher positioning accuracy of the Hall element can be obtained. Additionally, the number of parts to be used for the sensor can be reduced, and assembly of the parts can easily be carried out. The sensor, then, can have higher sensitivity and the parts thereof can readily and automatically be assembled.

The insulative film 5 has been applied onto a surface of the magnet 1 or flux guide 13 in this embodiment, however, if the magnet 1 or the flux guide 13 is insulative, there is no need to apply the insulative film 5 thereon. It is not intended that the material of the insulative film 5 be limited, and resin, glass, or ceramics such as alumina are suitable.

SECOND EMBODIMENT

Figure 5:
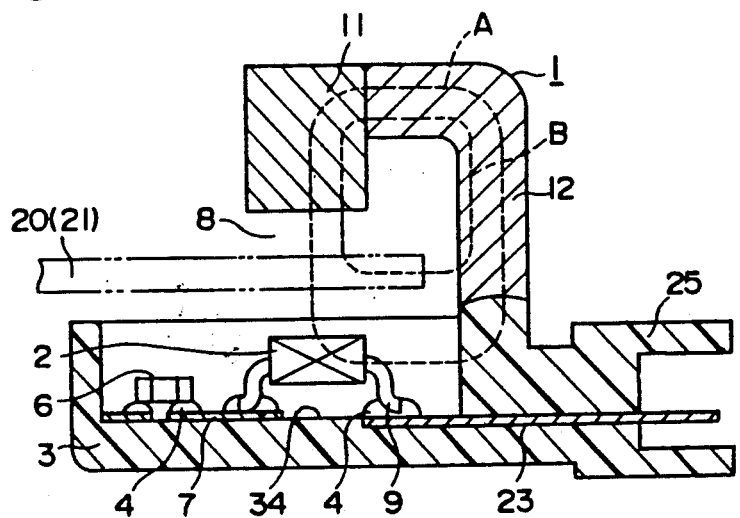
FIG. 5 is a sectional view of a Hall-effect sensor of a second embodiment of the present invention.
Figure 10:
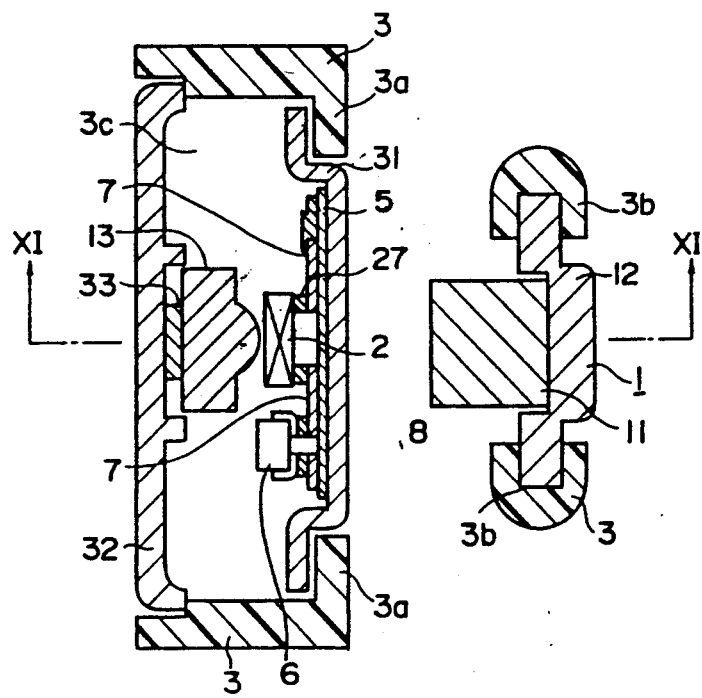
FIG. 10 is a sectional view of a Hall-effect sensor of a third embodiment of the present invention.
Figure 11:
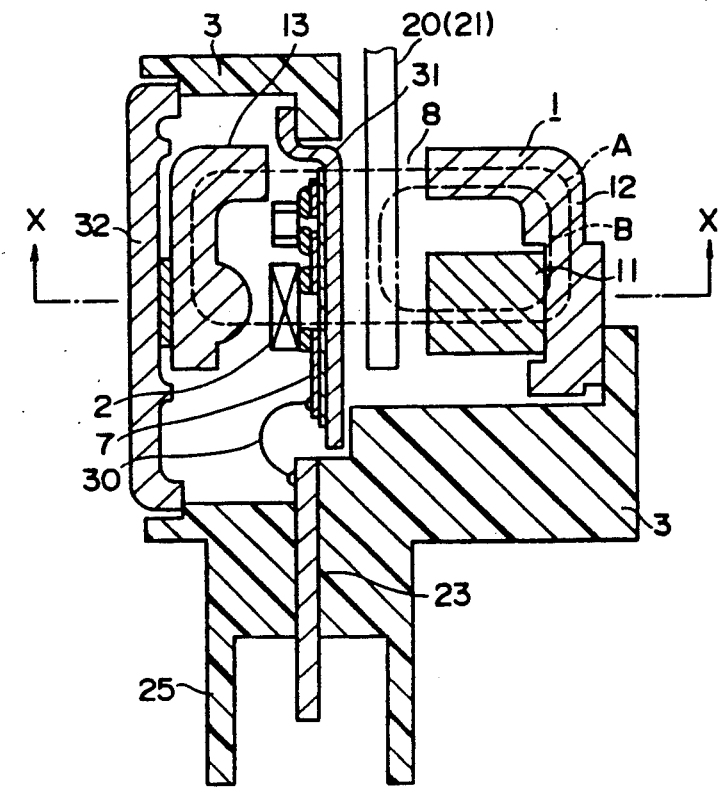
FIG. 11 is a sectional view of the Hall-effect sensor in FIG. 10 across line XI—XI.

FIG. 5 shows a sensor of the second embodiment. Reference numeral 1 in the figure shows a flux generating member which is comprised of a magnet 11 and a flux guide 12 which is kept in contact with the magnet 11. The flux generating member 1 is integrally locked to a molded frame 3 made of a mold resin. The molded frame 3 has a fixing portion 34 for fixing the Hall element 2. In the molded frame 3, there is fitted an insert conductor 23, which is connected to a printed conductor 7 being formed on the fixing portion 34 in the molded frame 3. At one end of the molded frame 3, there is formed a connector 25. The Hall element 2 is disposed in a position below the magnet 11 with a gap 8 between. A lead wire 9 of the Hall element 2 is electrically connected to the printed conductor 7 and to the insert conductor 23 by a soldering paste 4. An electronic part 6 such as a surge protection element is provided in the fixing portion 34 of the molded frame 3 with the soldering paste 4 between. An epoxy resin is filled in a space surrounding the Hall element 2 and the electronic part 6. When a temperature circumstance is severe, a silicon gel is filled in the space and a cover (a cover 32 as shown in FIGS. 10, 11) is provided in order to protect both of them.

Hereinbelow will be described the operation of the sensor. Such a flux shutter 20 as shown in FIG. 3 moves in the gap 8 in synchronism with rotation of an internal combustion engine. When the space 22 of the flux shutter 20 is positioned in the gap 8, a magnetic flux being generated by the magnetic 11 forms such a magnet path as shown by the broken line A. The magnetic flux being exerted upon the Hall element 2, thus is in the large state. On the other hand, when the vane 21 of the flux shutter 20 is positioned in the gap 8, a magnetic flux being generated by the magnet 11 forms such a magnetic path as shown by the broken line B. The magnetic flux exerted upon the Hall element 2, thus is in the small state. As can be seen from the above, such change of the magnetic flux in synchronism with the rotation of the internal combustion engine is given to the Hall element 2, and an electric signal corresponding to the change of the magnetic flux is generated according to the Hall effect. This electric signal is led to the outside circuit (not shown) via the printed conductor 7 and the insert conductor 23, and its waveform is processed to be used for detecting a crank angle.

Figure 6:
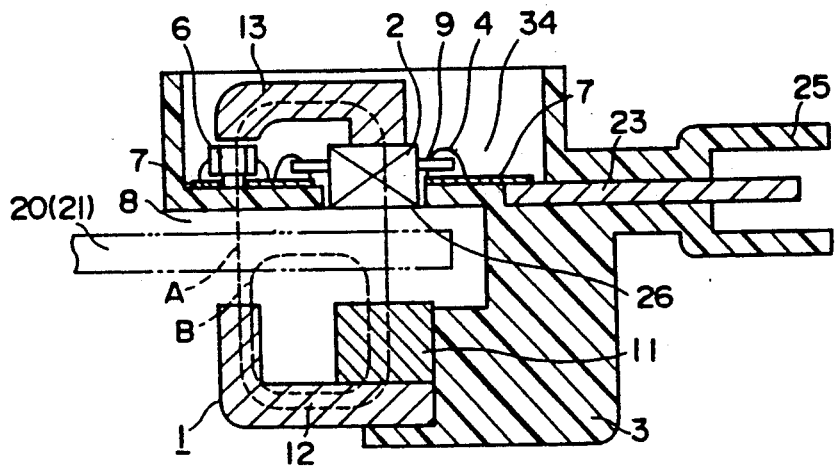
FIG. 6 is a sectional view of a Hall-effect sensor of one transformed example of the second embodiment of the present invention.

FIG. 6 shows a transformed example of the sensor of the second embodiment. As similar to the embodiment shown in FIG. 4, a flux guide 13, in this example, is provided so as to be in contact with a Hall element 2 and is fixed to the molded frame 3, which fixing is not shown in detail in the figure. The Hall element 2 is housed in a hole 26, which is formed to be through a fixing portion 34 of the molded frame 3. Other construction of this sensor being the same as that in FIG. 5, explanation of those elements numbered identically with those of the embodiment of FIG. 5 will be omitted here.

Hereinbelow will be described the operation of the sensor. When the space 22 of the flux shutter 20 is positioned in the gap 8, such a magnetic path as shown by the broken line A is formed and the magnetic flux exerted upon the Hall element 2 is in the large state. On the other hand, when the vane 21 of the flux shutter 20 is positioned in the gap 8, such a magnetic path as shown by the broken line B is formed and the magnetic flux exerted upon the Hall element 2 is in the small state. As can be seen from the above, such change of the magnetic flux in synchronism with rotation of the internal combustion engine is given to the Hall element 2, and an electric signal corresponding to the change of the magnetic flux is generated according to the Hall effect. This electric signal is led to the outside circuit (not shown) via the printed conductor 7 and the insert conductor 23, and its waveform is processed to be used for detecting a crank angle.

In such a transformed example as shown in FIG. 6, because there is provided the flux guide 13, a flux density for the Hall element 2 can be made to be larger in the magnetic path shown by the broken line A. Accordingly, the change of the magnetic flux for the Hall element 2 can be made to be larger when the flux shutter 20 moves. Additionally, the Hall element 2 is housed in the hole 26 in order to shorten the magnetic path in the gap 8, and thus detecting sensitivity of the sensor can greatly be improved. Moreover a signal accuracy against a change of temperature or voltage can be increased.

Figure 7:
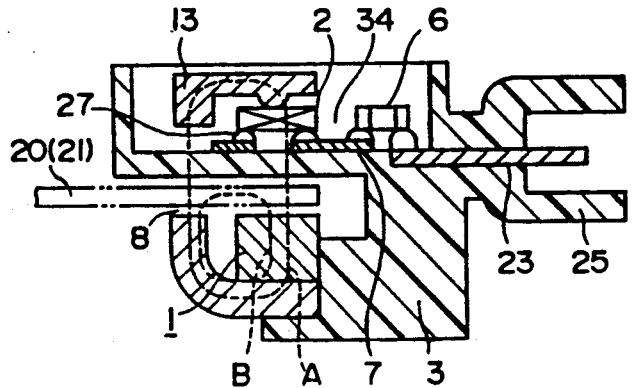
FIG. 7 is a sectional view of a Hall-effect sensor of another transformed example of the second embodiment of the present invention.

FIG. 7 shows another transformed example of the sensor of the second embodiment. In this example, a Hall element 2 of a Hall IC chip (flip chip) is electrically connected to a printed conductor 7 by a soldering bump 27. In this example, a substrate made of epoxy or alumina on which the Hall element 2 and the electronic part 6 are installed is needless. Accordingly, the magnetic path in the gap 8 is short, detecting sensitivity of the sensor can be improved in the same way as the example shown in FIG. 6. Other construction and operation of this sensor being the same as those of the sensor shown in FIG. 6, explanation of those elements numbered identically with those of the sensor in FIG. 6 will be omitted here.

Figure 8:
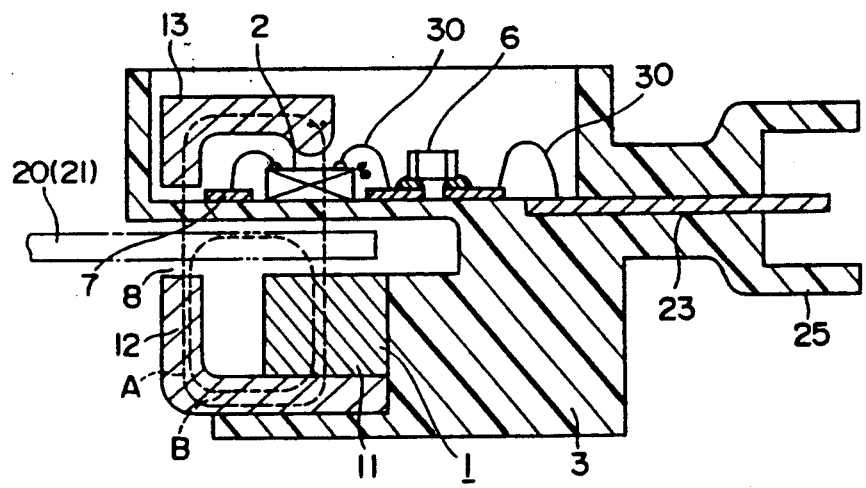
FIG. 8 is a sectional view of a Hall-effect sensor of a further transformed example of the second embodiment of the present invention.

FIG. 8 shows a further transformed example of the second embodiment. As the same as the embodiment shown in FIG. 7, a Hall element 2, in this example, is a Hall IC chip. The Hall element 2 is connected to a printed conductor 7, and so is the printed conductor 7 to an insert conductor 23 by a bonding wire 30, respectively, and the Hall element 2 is electrically connected to the insert conductor 23. Other construction being the same as the example shown in FIG. 7, explanation of those elements numbered identically with those of the embodiment in FIG. 7 will be omitted here. And an operation of this example is the same as that shown in FIG. 6.

Figure 9:
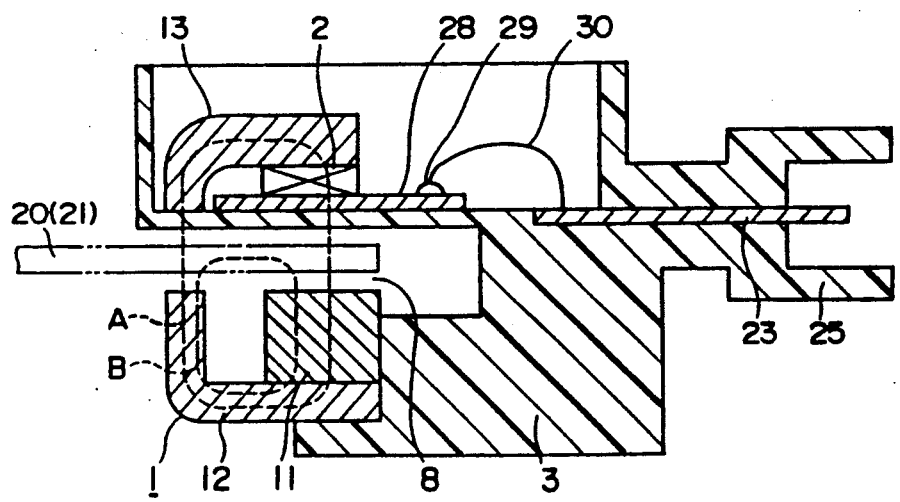
FIG. 9 is a sectional view of a Hall-effect sensor of a still further transformed example of the second embodiment of the present invention.

FIG. 9 shows a still further transformed example of the second embodiment. A Hall element 2, in this example, is a Hall IC. The Hall element 2 has a composition that a plurality of electronic parts and a printed circuit are provided onto a ceramic substrate 28. The Hall element 2 is provided with a plurality of terminal electrodes 29. Each terminal electrode 29 is connected to an insert conductor 23 by a bonding wire 30. As a suitable material for the bonding wire 30, gold, copper, aluminum, or alloy may be employed. Other construction and operation being the same as the sensor in another example of the second embodiment, explanation of those elements numbered identically with those of the sensor of another example will be omitted here.

In the second embodiment, the Hall element 2 being directly fixed to the molded frame 3, it is not necessary to provide a jig for positioning the Hall element 2. When the Hall element 2 is fixed to the molded frame 3, such an art as packaging a circuit element onto a printed wiring board is employed, and the sensor can position the Hall element with higher accuracy. Additionally, if an engaging projection and the like are formed in a fixing position for the Hall element 2 in the molded frame 3 in advance, for example, the Hall element 2 can readily be positioned with greater accuracy. Additionally, the number of parts to be used in the sensor can be reduced, and those parts can easily be assembled. Additionally, a sensor with greater sensitivity can be provided and parts of the sensor can readily and automatically be assembled. Furthermore, when the Hall element 2 is electrically connected to the insert conductor 23 by the bonding wire 30, it is not necessary to provide soldering. It is possible to provide a sensor which is resistant to mechanical vibration, and in which deformations of the printed conductor 7 and the insert conductor 23 according to expansion or contraction thereof on the basis of temperature change of the molded frame 3 are generated.

THIRD EMBODIMENT

FIGS. 10 and 11 show the third embodiment. In those figures, reference numeral 1 designates a flux generating member which is comprised of a magnet 11, a flux guide 12, a a flux guide 13. This flux generating member 1 is integrally positioned and locked in a molded frame 3. The molded frame 3 has a locking portion 3a for a plate 31, a locking portion 3b for the flux generating member 1 (flux guide 12), and a housing portion 3c for a Hall element 2 and the like. An insert conductor 23 is fitted in the molded frame 3, and at one end of the molded frame 3, there is formed a connector 25. The plate 31 made of metal, plastic or the like is arranged in a position to face the magnet 11 with a gap 8 between and is locked to the locking portion 3a. On the other surface of the plate 31 which is not facing the magnet 11, there is applied an insulative film 5, onto which is formed a printed conductor 7. The Hall element 2 and such an electronic part 6 as a surge protection element are connected to the printed conductor 7 by a soldering bump 27. The printed conductor 7 is electrically connected to the insert conductor 23 by a bonding wire 30. The flux guide 12 is positioned and locked in the locking portion 3b of the molded frame 3. The flux guide 13 is firmly fixed to a cover 32 by an adhesive agent 33. The cover 32 for covering the housing portion 3c is fixed to the molded frame 3. A resin such as a silicon gel is filled into a space surrounding the Hall element 2 and the flux guide 13 in the housing portion 3c in order to protect both of them from their surroundings.

Hereinbelow will be described the operation of the sensor. Such a flux shutter 20 as shown in FIG. 3 moves in the gap 8 in synchronism with rotation of the internal combustion engine. When the space 22 of the flux shutter 20 is positioned in the gap 8, a magnetic flux being generated by the magnet 11 forms such a magnetic path as shown by the broken line A in FIG. 11. The magnetic flux exerted upon the Hall element 2 thus is in the large state. On the other hand, when the vane 21 of the flux shutter 20 is positioned in the gap 8, a magnetic flux being generated by the magnet 11 forms such a magnetic path as shown by the broken line B in FIG. 11. The magnetic flux exerted upon the Hall element 2 thus is in the small state. As can be seen from the above, such change of the magnetic flux in synchronism with the rotation of the internal combustion engine is given to the Hall element 2, and an electric signal corresponding to the change of the magnetic flux is generated according to the Hall effect. This electric signal is led to the outside circuit (not shown) through the insert conductor 23, and its waveform is processed to be used for detecting a crank angle.

In the third embodiment, the Hall element 2 is positioned and fixed to the molded frame 3 via the plate 31, then, it is not necessary to provide a jig for positioning the Hall element 2. The Hall element 2 is positioned by being fixed to the soldering bump 27. This fixing can readily be carried out with higher positioning accuracy with an assembly robot, for example. The molded frame 3 has a limit size of thickness. In the third embodiment, the plate 31 made of metal or plastic is used, it is easy to make the plate 31 thin, so the magnetic path in the gap 8 can be short. As a result, it can be realized to provide a sensor with higher sensitivity and automatic assembly of the parts can easily be performed.

The insulative film 5 and the printed conductor 7 are formed on the plate 31 in the third embodiment, however, those may not necessarily be formed. When an insulative material is used for the material of the plate 31, it is not necessary to apply the insulative film 5, and in addition, when a Hall IC is used as the a Hall element 2, it is not necessary to provide the printed conductor 7, either.

In such embodiments as mentioned above, explanation has been made for when the sensor is used so as to detect a crank angle for ignition timing control for internal combustion engine. However, the sensor may be employed as other sensors such as a position sensor or a speed sensor. In addition, the flux shutter 20 may not be adapted to be rotated but may be adapted to be moved linearly. It is not intended that configuration of the flux shutter 20 be limited to that shown in FIG. 3.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within the metes and bounds of the claims, or equivalence of such metes and bounds thereof are therefore intended to be embraced by the claims.

What is claimed is:

1. A Hall-effect sensor, comprising:
flux generating means for generating a magnetic flux,
a Hall element disposed in the path of said magnetic flux,
positioning and fixing means for positioning and fixing said Hall element and holding said flux generating means and said Hall element integrally therewith, said positioning and fixing means comprising a molded frame having a fixing portion, wherein said fixing portion is formed in advance in said molded frame,
a printed conductor being formed on said fixing portion of said molded frame,
an insert conductor fitted within said molded frame and coupled to said fixing portion of said molded frame and arranged to receive an output signal from said Hall element, and
a peripheral circuit means positioned in said fixing portion of said molded frame, said peripheral circuit means performing an electronic function for said Hall element and being fixed to said printed conductor to be connected to said Hall element, said Hall element being fixed to said fixing portion and connected to said printed conductor.

2. A Hall-effect sensor as set forth in claim 1, further comprising:
connecting means for electrically connecting said Hall element to said printed conductor, wherein said connecting means are positioned between said Hall element and said printed conductor.

3. A Hall-effect sensor as set forth in claim 2, wherein said connecting means is a bonding wire.

4. A Hall-effect sensor as set forth in claim 2, wherein said connecting means is solder.

5. A Hall-effect sensor as set forth in claim 1, wherein said flux generating means has a magnet for generating a magnetic flux and a flux guide for transmitting the generated magnetic flux.

6. A Hall-effect sensor as set forth in claim 1, wherein said Hall element is a bare Hall chip.

7. A Hall-effect sensor as set forth in claim 6, wherein said Hall chip is a Hall IC.

* * * * *

REEXAMINATION CERTIFICATE (4234th)

United States Patent [19]
Murata

[11] B1 5,093,617
[45] Certificate Issued Dec. 19, 2000

[54] HALL-EFFECT SENSOR HAVING INTEGRALLY MOLDED FRAME WITH PRINTED CONDUCTOR THEREON

[75] Inventor: Shigemi Murata, Himeji, Japan

[73] Assignee: Mitsubishi Denki Kabushiki Kaisha, Tokyo, Japan

Reexamination Request:
No. 90/005,528, Oct. 6, 1999

Reexamination Certificate for:
Patent No.: 5,093,617
Issued: Mar. 3, 1992
Appl. No.: 07/493,526
Filed: Mar. 14, 1990

[30] Foreign Application Priority Data

| Mar. 14, 1989 | [JP] | Japan | 1-59539 |
| Mar. 15, 1989 | [JP] | Japan | 1-60706 |
| Mar. 15, 1989 | [JP] | Japan | 1-60707 |
| Mar. 15, 1989 | [JP] | Japan | 1-60708 |
| Mar. 15, 1989 | [JP] | Japan | 1-60709 |

[51] Int. Cl.[7] .................. G01B 7/30; F02P 7/07; G01R 33/07
[52] U.S. Cl. .................. 324/235; 324/207.2; 324/251; 123/146.5 A; 123/617
[58] Field of Search ..................... 324/173, 174, 324/207.2, 207.21, 207.25, 235, 251, 252; 123/617, 146.5 A, 406.52, 406.58

[56] References Cited

U.S. PATENT DOCUMENTS

4,235,213  11/1980  Jellissen ..................... 123/146.5 A

FOREIGN PATENT DOCUMENTS

| 30 01 771 | 7/1981 | Germany | H03K 17/95 |
| 29 33 557 | 11/1982 | Germany | G01D 5/12 |
| 32 26 073 | 4/1983 | Germany | G01P 3/487 |
| 8604291 | 8/1986 | Germany | B60K 26/02 |
| 90-5346 | 8/1989 | Rep. of Korea | G01B 7/30 |
| 611 038 | 5/1979 | Switzerland | G01R 33/06 |

OTHER PUBLICATIONS

Ulrich Lachmann, "Function and Use of the Hall–Effect Vane Switch HKZ 101", Siemens Components 20 (1982) Book 3, pp. 73–75.

E. Zabler and P. Heintz, "New Alternative Solutions for Rotational Speed Sensors in the Motor Vehicle on a Magneto–resistance Basics", VDI–Berichte Nr. 509, 1984, pp. 263–268.

Arnold et al; Hall Effect Detector and Miniswitch, IBM Technical Disclosure Bulletin, vol. 17, No. 11, p. 3220, Apr. 1975.

*Primary Examiner*—Gerard R Strecker

[57] ABSTRACT

A Hall-effect sensor, wherein a Hall element is disposed in a magnetic path being formed by a magnet and a flux guide, and the magnet, flux guide, and Hall element are integrally held with a molded frame, and the Hall element is fixed to the magnet (or flux guide) or the molded frame. This Hall-effect sensor can easily position the Hall element with higher sensitivity.

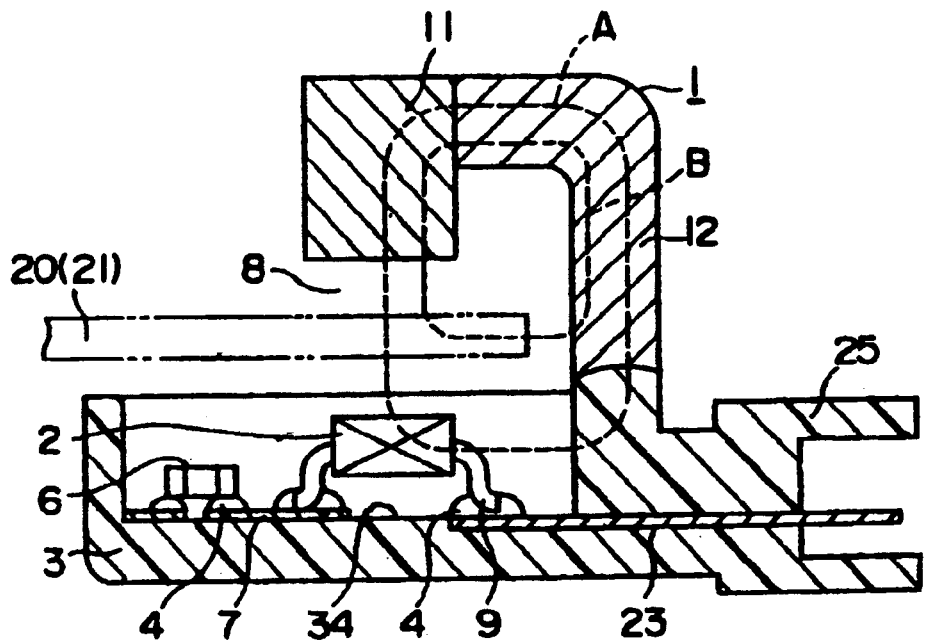

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 through 7 is confirmed.

* * * * *